United States Patent
Nation et al.

(10) Patent No.: US 10,429,284 B1
(45) Date of Patent: Oct. 1, 2019

(54) IN SITU ENVIRONMENTALLY-ISOLATED WEAR TESTER

(71) Applicant: National Technology & Engineering Solutions of Sandia, LLC, Albuquerque, NM (US)

(72) Inventors: Brendan L. Nation, Albuquerque, NM (US); Nicolas Argibay, Albuquerque, NM (US)

(73) Assignee: National Technology & Engineering Solutions of Sandia, LLC, Albuquerque, NM (US)

(*) Notice: Subject to any disclaimer, the term of this patent is extended or adjusted under 35 U.S.C. 154(b) by 148 days.

(21) Appl. No.: 15/659,467

(22) Filed: Jul. 25, 2017

Related U.S. Application Data

(60) Provisional application No. 62/368,077, filed on Jul. 28, 2016.

(51) Int. Cl.
*G01N 3/56* (2006.01)
*G01N 19/02* (2006.01)

(52) U.S. Cl.
CPC ........... *G01N 3/56* (2013.01); *G01N 19/02* (2013.01)

(58) Field of Classification Search
CPC ................................. G01N 3/56; G01N 19/02
USPC ............................................................. 73/9
See application file for complete search history.

(56) References Cited

U.S. PATENT DOCUMENTS

| | | | | |
|---|---|---|---|---|
| 5,455,420 A | * | 10/1995 | Ho | G01Q 30/02 250/442.11 |
| 6,259,960 B1 | * | 7/2001 | Inokuchi | G01N 21/9501 250/310 |
| 6,349,587 B1 | * | 2/2002 | Mani | G01N 19/02 73/9 |
| 7,490,010 B2 | * | 2/2009 | Osada | G05B 19/41875 700/108 |
| 7,574,932 B2 | * | 8/2009 | Hasuda | G03F 1/72 250/442.11 |
| 9,574,080 B1 | * | 2/2017 | Street | C08L 63/00 |
| 2002/0195555 A1 | * | 12/2002 | Weinberger | H01J 49/004 250/281 |
| 2009/0087932 A1 | * | 4/2009 | Kondoh | H01L 21/67196 438/30 |
| 2014/0241611 A1 | * | 8/2014 | Isomura | G06T 7/0008 382/149 |
| 2019/0033256 A1 | * | 1/2019 | Matsushita | G01N 27/62 |

FOREIGN PATENT DOCUMENTS

DE 10203070 A1 * 7/2003 ............. G01N 19/02

OTHER PUBLICATIONS

Translation of Boerner et al (DE 10203070 A1) (Year: 2003).*
Argibay, N. et al., "Asymmetric wear behavior of self-mated copper fiber brush and slip-ring sliding electrical contacts in a humid carbon dioxide environment", Wear, vol. 268, Issues 3-4 (2010), pp. 455-463.

(Continued)

*Primary Examiner* — Nathaniel T Woodward
(74) *Attorney, Agent, or Firm* — Helen S. Baca

(57) ABSTRACT

The present invention relates to an in situ testing system, which includes a wear tester and an enclosure. The wear tester is configured to apply a normal load, by way of a tip, to a surface of the test sample. Use of an enclosure allows such wear testing to be conducted in a controlled environment.

20 Claims, 3 Drawing Sheets

(56) References Cited

OTHER PUBLICATIONS

Bares, J.A. et al., "High current density copper-on-copper sliding electrical contacts at low sliding velocities", Wear, vol. 267, Issues 1-4 (2009), pp. 417-424.

Keith, J.H., "Design of a Pin-on-Disk Tribometer with In Situ Optical Profilometry", thesis presented to the Graduate School of the University of Florida (2010), 27 pages.

Babuska TF et al., "Temperature-dependent friction and wear behavior of PTFE and $MoS_2$," Tribol. Lett. 2016;63:15 (7 pp.).

Curry JF et al., "Highly oriented $MoS_2$ coatings: tribology and environmental stability," Tribol. Lett. 2016;64:11 (9 pp.).

Curry JF et al., "Temperature-dependent friction and wear of $MoS_2/Sb_2O_3/Au$ nanocomposites," Tribol. Lett. 2016;64:18 (5 pp.).

Nation BL et al., "In-situ testing: an exploration of increasing design complexity," Sandia Report No. SAND2015-10978C, Dec. 2015 (21 pp.).

\* cited by examiner

IN SITU ENVIRONMENTALLY-ISOLATED WEAR TESTER

CROSS-REFERENCE TO RELATED APPLICATION

This application claims the benefit of U.S. Provisional Application No. 62/368,077, filed Jul. 28, 2016, which is hereby incorporated by reference in its entirety.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates to an in situ testing system, which includes a wear tester and an enclosure. The wear tester is configured to apply a normal load, by way of a tip, to a surface of the test sample. Use of an enclosure allows such wear testing to be conducted in a controlled environment.

BACKGROUND OF THE INVENTION

Tribological properties of a material can provide insightful design information. Accurate properties can be employed to predict aging effects upon certain materials. In particular, there is need to for system that allow for in situ testing of materials in a controlled manner.

SUMMARY OF THE INVENTION

The present invention relates to a wear testing system, which includes an enclosure (e.g., a portable enclosure) that provides a controlled environment during sample testing. Accordingly, in one aspect, the present invention features an in situ testing system including a wear tester and an enclosure configured to house the tester.

In one instance, the wear tester includes a sample mount configured to hold a sample; a first positioner configured to position the sample mount; a tip configured to contact a surface of the sample; and a load cell configured to apply a normal load to the tip and to measure a friction arising from contact between the tip and the surface of the sample.

In another instance, the enclosure includes a base plate; a plurality of side walls and a top wall configured to provide an internal chamber; a sealing surface formed between a portion of the surface of the base plate and an edge of each of the plurality of side walls; and a vacuum exchange port configured to introduce an additional sample to the tester without changing an environment maintained within the internal chamber. Additional details follows.

Definitions

As used herein, the term "about" means +/−10% of any recited value. As used herein, this term modifies any recited value, range of values, or endpoints of one or more ranges.

By "fluidic communication," as used herein, refers to any duct, channel, tube, pipe, chamber, or pathway through which a substance, such as a liquid, gas, or solid may pass substantially unrestricted when the pathway is open. When the pathway is closed, the substance is substantially restricted from passing through. Typically, limited diffusion of a substance through the material of a plate, base, and/or a substrate, which may or may not occur depending on the compositions of the substance and materials, does not constitute fluidic communication.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the invention will be apparent from the following description and the claims.

DETAILED DESCRIPTION OF THE INVENTION

The present invention relates to an in situ wear testing system, which includes a wear tester and an enclosure configured to house the tester. Any type of wear can be induced and characterized by the system, including friction, abrasion, lubrication effects on wear, etc. Such effects can be determined by any useful surface detector, e.g., an interferometer (e.g., a scanning white light interferometer or SWLI), an atomic force microscope, a Raman/Fourier Transform Infrared (FTIR) spectroscopy unit, an optical microscope, etc.

Figure 1:
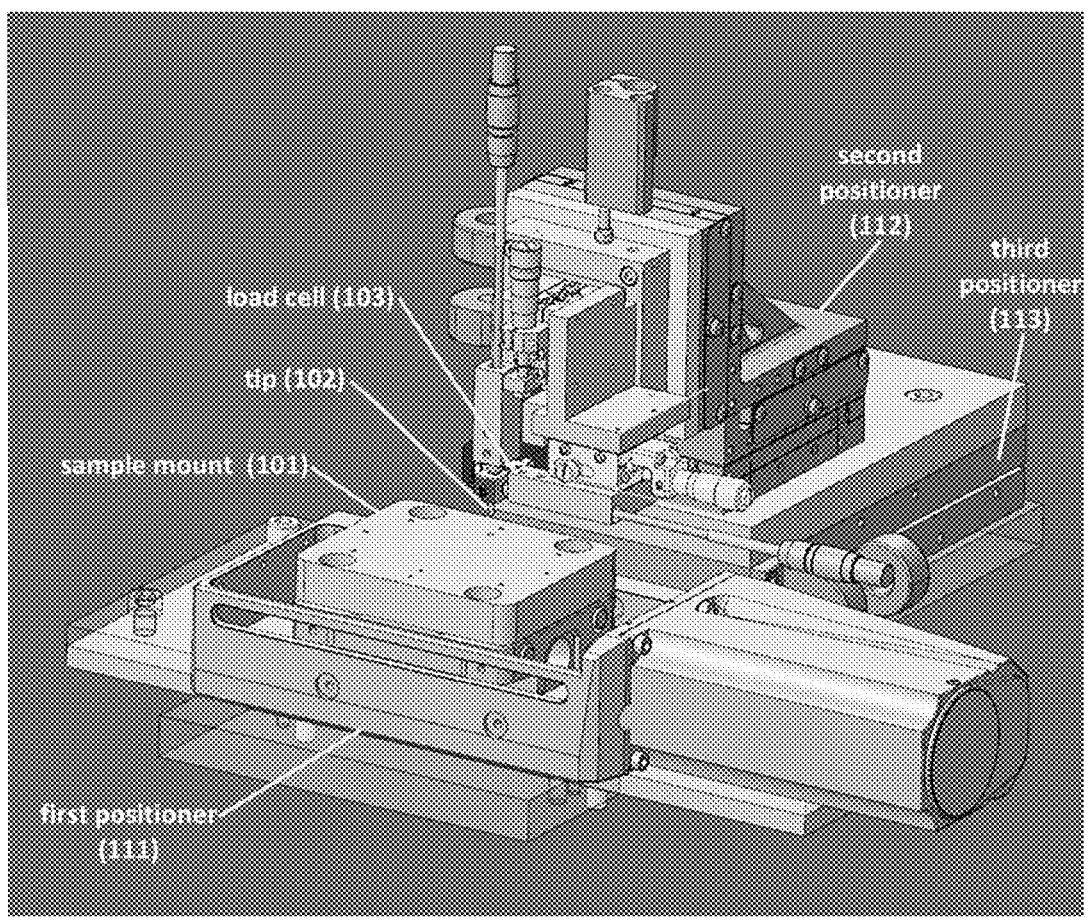
FIG. 1 provides a schematic of an exemplary wear tester having a first positioner 111 configured to provide linear translation of the sample mount 101.

The wear tester can be configured in any useful manner. FIG. 1 provides an exemplary, non-limiting tester including a sample mount 101 configured to hold a sample and a first positioner 111 configured to position the sample mount. The first positioner can move in any useful manner, including linear translation (e.g., as for a linear tribometer) and/or rotational motion. In this way, different types of wear can be induced upon the surface of the sample. The sample mount can be formed from any useful material (e.g., a polymer, such as PEEK or PTFE). A load can be applied to a surface of the sample by way of a tip 102 configured to contact or engage the surface, as well as a load cell 103 configured to apply a normal load to the tip. The load cell can be further configured to measure a force (e.g., friction force) arising from the interaction between the tip and the surface of the sample. The load cell and/or the tip can be positioned in any useful manner. In some instances, these components can be positioned by employing a second positioner 112 configured to provide fine positioning of the load cell and/or tip (e.g., by allowing for manual adjustment), as well as a third positioner 113 configured to provide positioning over a larger range of distance (e.g., by employing a powered actuator).

Figure 2:
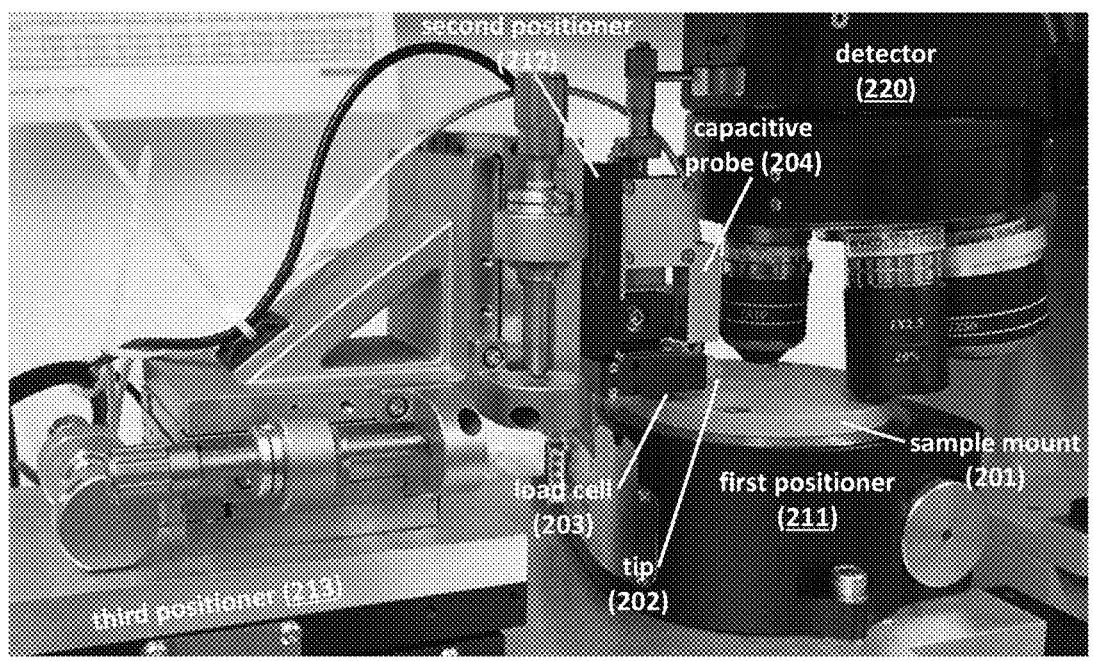
FIG. 2 provides a photograph of an exemplary wear tester having a first positioner 211 configured to provide rotational motion of the sample mount 201.

In another instance, the tester can be configured to rotate the sample. FIG. 2 provides a tester including a sample mount 201 and a first positioner 211 configured to position the sample mount (e.g., by way of a rotary stage configured to rotate the sample). The tester also includes a tip 202 configured to engage a surface of the sample, a load cell 203 configured to apply and measure the load (e.g., a cantilever-style, multi-axis load cell), and a capacitive probe 204 (optionally on an adjustable mount) configured to read the load cell. The tester can include any useful positioner (e.g., a first positioner 211 configured to position the sample mount, a second positioner 212 configured to position the load cell (e.g., a z-stage piezoelectric positioner for positioning and loading the cantilever-style load cell), and a third positioner 213 configured to position the load cell and/or tip). The tester can be configured to work with a detector 220 to provide surface characteristics of the sample during wear testing.

Figure 3A:
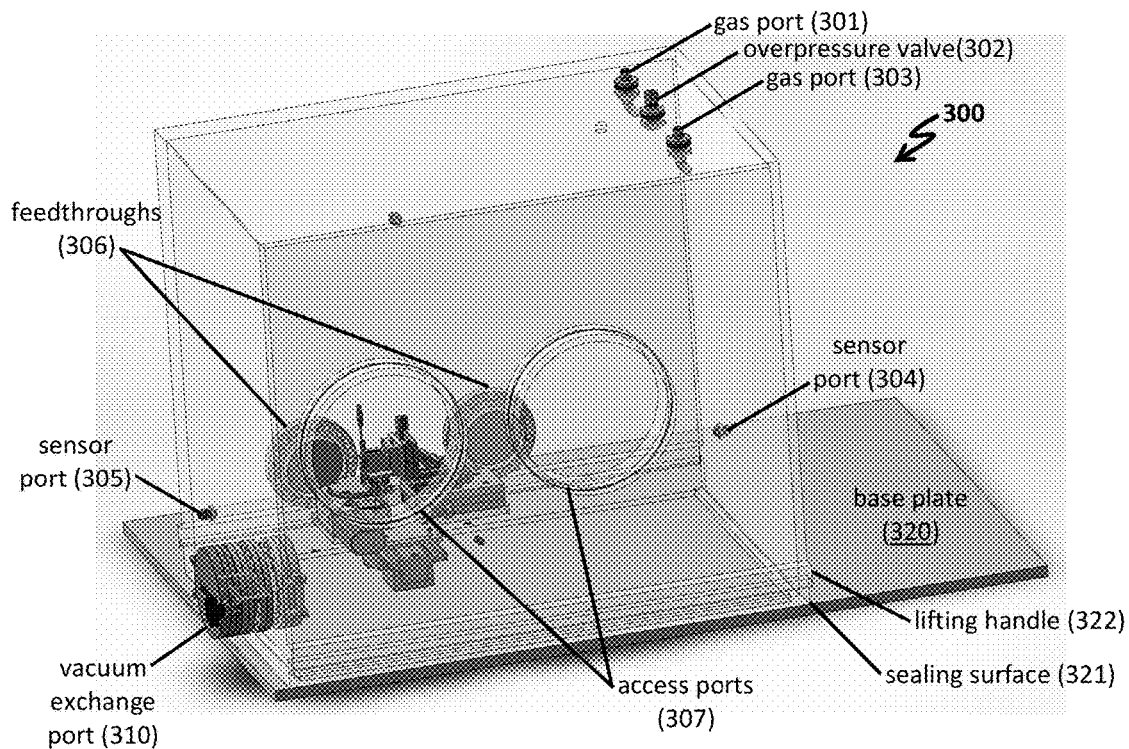
FIG. 3A-3B provides schematics of an exemplary system 300 including an enclosure disposed upon a base plate 320 (FIG. 3A) and a close-up view of a portion of an enclosure including various feedthroughs, including one or more bus ports 351, data ports 352, and connector ports 353 (FIG. 3B).

The system can further include an enclosure configured to house the tester. FIG. 3A provides an exemplary, non-limiting embodiment of a system 300 including an enclosure. The enclosure can include a plurality of side walls and a top wall configured to provide an internal chamber. As seen in FIG. 3A, the side walls are vertical, and the top wall is horizontal and includes various gas ports 301,303 (e.g., inlets for inert gas, such as nitrogen) and valves 302 (e.g., configured as an overpressure valve that released the gas within the internal chamber upon exceeding a threshold pressure). The vertical side walls can include any useful number of components (e.g., ports, sensors, and/or feedthroughs) to facilitate use of the wear tester. As can be seen, the side walls can include sensor ports 304,305 (e.g., closed loop sensor ports, such as for oxygen and/or moisture sensing), feedthroughs 306, and access ports 307.

The enclosure can include a base plate 320 configured to engage an edge of the vertical side walls and provide a sealing surface 321. The enclosure can include a lifting handle 322 to allow the vertical side walls and top wall to be placed upon the base plate 320, in which the weight of the walls form the sealing surface 321. The combination of the vertical side walls, top horizontal wall, and the base plate forms an internal chamber for the enclosure.

Figure 3B:
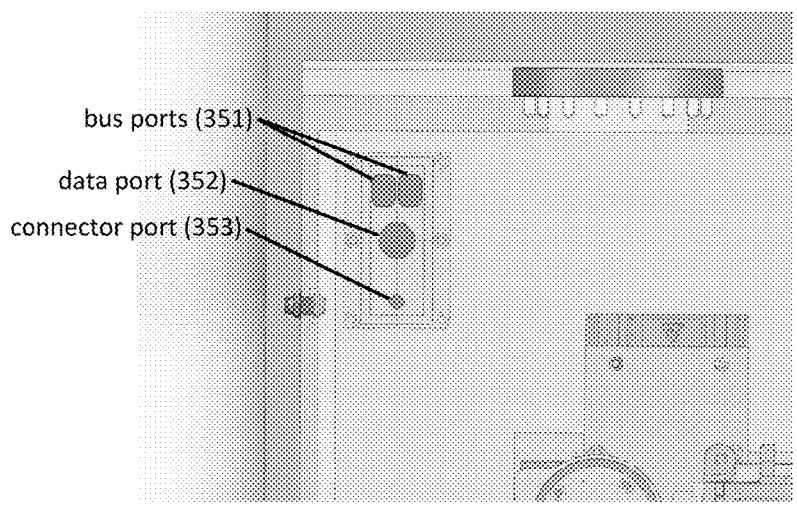

The enclosure can include any other useful components. In one instance, the enclosure can include a control box configured to allow the operator to control purge functions of one or more gases within the internal chamber of the enclosure. In another instance, the enclosure can include a vacuum exchange port configured to introduce samples into the enclosure without disrupting the established environment within the internal chamber. In yet another instance, the enclosure can include instrumentation feedthroughs. FIG. 3B provides exemplary feedthroughs that can be disposed in any position of the enclosure (e.g., within a vertical wall or a horizontal wall). Such feedthroughs can include one or more bus ports 351 (e.g., USB ports), data ports 352 (e.g., Ethernet ports), and/or connector ports 353 (e.g., pin-type connectors, wire connectors, cords, etc.)

Example

An in situ wear tester was developed to be coupled to a non-contact surface detector (e.g., an interferometer, such as a scanning white light interferometer or SWLI). The SWLI allows for measurements of wear in a highly accurate manner. The entire apparatus is modular and can be shielded using a specially designed glovebox made to encompass both the wear tester and the detector. The wear tester can be used outside of the glovebox and SWLI for standard wear measurements.

The wear tester can be employed to determine the effect of load pressure on a sample. In one instance, the wear tester includes a rigid mount configured to hold the sample (e.g., a polyether ether ketone or PEEK sample mount) and a sample positioner employed to move the mount (with the sample) in a controlled manner. Such sample positioners can move the mount in a rotary and/or a linear fashion. As the sample positioner moves the sample, a tip is configured to contact a surface of the sample. The tip can have any useful configuration, e.g., a spherical pin or ball.

By applying a normal load to the tip, wear is induced upon the surface. The wear track is controlled by the movement of the positioner. A load cell (e.g., a flexible cantilever-style load cell) can be employed to apply the normal load on the tip and to measure the resulting friction force during movement. The tip, as well as the load cell, can be provided on another positioner or a plurality of positioners, thereby providing refined positioning of the tip and/or load cell upon the sample.

When employed with a surface detector (e.g., an interferometer), the positioners can be employed as to allow interferometry data to be captured during movement. This allows for the wear track (resulting from the frictional contact between the tip and the sample during movement) to be imaged during all phases of the test, thus allowing the operator to characterize the evolution of the wear behavior during frictional loading.

Optionally, an enclosure can be employed with the wear tester. In one instance, a custom glovebox was designed to allow the tester and the surface detector to be shielded from the ambient environment. Furthermore, the enclosure allows the testing environment to be controlled, e.g., by way of an inert gas purge, evacuation, and/or flow-through method. The enclosure can include any useful components to maintain the test environment, such as a vacuum exchange chamber configured to be in fluidic communication with the enclosure, yet be accessible by way of an external port. In this way, an operator can introduce a sample into the vacuum exchange chamber without breaking the atmosphere within the enclosure, such as by inserting the sample into the exchange chamber, pumping it down and purging with an inert gas, and then introducing it into the interior chamber of the enclosure. By using such an exchange chamber, the test environment can be maintained within the enclosure, but new samples can still be introduced to the wear tester. The small footprint of the enclosure with the vacuum exchange chambers allows for a portable system.

The enclosure also employs a flat base plate as its bottom surface. A seal is formed by placing a sealing strip between the walls of the enclosure and the base plate. The sealing strip is designed to seal against a base plate using the weight of the enclosure. The enclosure is protected from overpressure via a ball-and-fitting device. The fitting is sized to allow a ball to sit on top of it, creating a light seal so that oxygen and moisture cannot travel into the glovebox. However, once a calculated pressure is exceeded, the ball lifts and allows the pressure to decrease quickly. This method enables the glovebox to be overpressure protected at very low pressures (e.g., of from about 0.1 to about 0.3 psi). If a sizable overpressure situation occurs, then the enclosure can lift slightly off of the base plate and allow pressurized gas to escape.

The enclosure also includes custom designed feedthroughs to allow the wear tester and the enclosure to be used together or separately, even when the wear tester is not mounted on the surface detector. Other feedthroughs include those configured to connect one or more power sources or instrumentation sources, such as bus ports (e.g., USB ports), data ports (e.g., Ethernet ports), and/or connector ports (e.g., for power sources or pins).

The enclosure can also feature a control box that uses electronic solenoids to control the flow of inert gas purge and exhaust into and out of the enclosure. In this way, the control box can be employed to inject an inert gas into the enclosure (e.g., by opening an injection port), to evacuate the gas out of the enclosure (e.g., by opening an exhaust port), and to continuously flow gas through the enclosure (e.g., by opening both the injection port and the exhaust port). These modes can be employed to instill desired test conditions, such as controlled oxygen content (e.g., low oxygen content), controlled humidity (e.g., low humidity), and/or controlled pressure within the enclosure. Any useful fluid can be employed with the enclosure, including an inert gas, oxygen, nitrogen, argon, etc.

Yet another feature of the system includes a remote unit inside of the enclosure that allows the operator to perform various functions while working within the enclosure. Such functions can include those described herein for the control box. Each of these functions can be represented by a button, such as a first button that allows an inert gas to pressurize the enclosure (a purge mode), a second button that allows an exhaust port to open and thereby suctioning gas out of the enclosure (a evacuate mode), and a third button that allows an injection port and an exhaust port to flow into the enclosure with negligible increases in pressure within the enclosure (a flow mode). In one non-limiting embodiment, the remote unit can include three buttons or switches connected to an umbilical. The control units can be designed to allow alternating use of the internal remote unit and the external control box without causing electrical problems.

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. An in situ testing system comprising:
   a wear tester, wherein the tester comprises:
      a sample mount configured to hold a sample;
      a first positioner configured to position the sample mount;
      a tip configured to contact a surface of the sample; and
      a load cell configured to apply a normal load to the tip and to measure a friction arising from contact between the tip and the surface of the sample; and
   an enclosure configured to house the tester, wherein the enclosure comprises:
      a base plate;
      a plurality of side walls and a top wall configured to provide an internal chamber;
      a sealing surface formed between a portion of the surface of the base plate and an edge of each of the plurality of side walls;
      a vacuum exchange port configured to introduce an additional sample to the tester without changing an environment maintained within the internal chamber; and
      an overpressure valve configured to release one or more fluids within the internal chamber of the enclosure.

2. The system of claim 1, wherein the tester further comprises:
   one or more capacitive probes configured to measure one or more electrical signals transmitted by the load cell.

3. The system of claim 1, wherein the load cell is a cantilever load cell.

4. The system of claim 1, wherein the tip comprises a spherical ball or spherical pin.

5. The system of claim 1, wherein the tester further comprises:
   a second positioner configured to position the tip and/or the load cell relative to the sample mount.

6. The system of claim 1, further comprising:
   a surface detector configured to measure one or more surface measurements of the sample during contact with the tip.

7. The system of claim 6, wherein the surface detector comprises an interferometer.

8. The system of claim 1, wherein the first positioner is configured to provide rotational movement and/or linear movement of the sample.

9. The system of claim 8, wherein the first positioner comprises a rotary stage.

10. The system of claim 8, wherein the first positioner comprises a linear translation stage.

11. The system of claim 1, wherein the enclosure further comprises:
    one or more feedthroughs disposed within at least one of plurality of side walls and/or the top wall of the enclosure, wherein at least on feedthrough is configured to provide one or more power sources or instrumentation sources.

12. The system of claim 1, wherein at least one of the one or more fluids is selected from the group consisting of oxygen, nitrogen, argon, an inert gas, as well as mixtures thereof.

13. The system of claim 1, wherein the enclosure further comprises:
    a lifting handle disposed above the sealing surface.

14. An in situ testing system comprising:
    a wear tester, wherein the tester comprises:
       a sample mount configured to hold a sample;
       a first positioner configured to position the sample mount
       a tip configured to contact a surface of the sample; and
       a load cell configured to apply a normal load to the tip and to measure a friction arising from contact between the tip and the surface of the sample;
    an enclosure configured to house the tester, wherein the enclosure comprises:
       a base plate;
       a plurality of side walls and a top wall configured to provide an internal chamber;
       a sealing surface formed between a portion of the surface of the base plate and an edge of each of the plurality of side walls; and a vacuum exchange port configured to introduce an additional sample to the tester without changing an environment maintained within the internal chamber; and a remote control box unit disposed within the internal chamber of the enclosure, wherein the remote control box unit is configured to open and close one or more ports configured to deliver a fluid into or out of the internal chamber.

15. The system of claim 14, further comprising:
an external control box unit disposed outside of the enclosure, wherein the external control box unit is configured to open and close one or more ports configured to deliver a fluid into or out of the internal chamber.

16. The system of claim 14, wherein the enclosure further comprises:
one or more feedthroughs disposed within at least one of plurality of side walls and/or the top wall of the enclosure, wherein at least on feedthrough is configured to provide one or more power sources or instrumentation sources.

17. An in situ testing system comprising:
a wear tester, wherein the tester comprises:
   a sample mount configured to hold a sample;
   a first positioner configured to position the sample mount;
   a tip configured to contact a surface of the sample;
   a load cell configured to apply a normal load to the tip and to measure a friction arising from contact between the tip and the surface of the sample; and
   one or more capacitive probes configured to measure one or more electrical signals transmitted by the load cell;

an enclosure configured to house the tester, wherein the enclosure comprises:
   a base plate;
   a plurality of side walls and a top wall configured to provide an internal chamber;
   a sealing surface formed between a portion of the surface of the base plate and an edge of each of the plurality of side walls; and
   a vacuum exchange port configured to introduce an additional sample to the tester without changing an environment maintained within the internal chamber;

a remote control box unit disposed within the internal chamber of the enclosure, wherein the remote control box unit is configured to open and close one or more ports configured to deliver a fluid into or out of the internal chamber; and an external control box unit disposed outside of the enclosure, wherein the external control box unit is configured to open and close one or more ports configured to deliver a fluid into or out of the internal chamber.

18. The system of claim 17, wherein the tester is a tribometer.

19. The system of claim 17, further comprising one or more temperature sensors, pressure sensors, oxygen sensors, moisture sensors, valves, and/or ports.

20. The system of 17, further comprising:
a surface detector configured to measure one or more surface measurements of the sample during contact with the tip.

* * * * *